(12) United States Patent
Baldinger

(10) Patent No.: US 7,838,526 B2
(45) Date of Patent: Nov. 23, 2010

(54) METHOD OF TREATING NEUROLOGICAL DISORDERS

(76) Inventor: Esther Baldinger, 8118 21st Ave., Brooklyn, NY (US) 11214-2504

(*) Notice: Subject to any disclaimer, the term of this patent is extended or adjusted under 35 U.S.C. 154(b) by 1138 days.

(21) Appl. No.: 11/489,998

(22) Filed: Jul. 20, 2006

(65) Prior Publication Data

US 2007/0031394 A1    Feb. 8, 2007

Related U.S. Application Data

(60) Provisional application No. 60/705,877, filed on Aug. 5, 2005.

(51) Int. Cl.
A61K 31/195 (2006.01)
A61K 31/44 (2006.01)
A61K 31/525 (2006.01)
A61K 31/51 (2006.01)

(52) U.S. Cl. .................. 514/251; 514/276; 514/350; 514/356; 514/561

(58) Field of Classification Search ........... 514/251, 514/276, 350, 561
See application file for complete search history.

(56) References Cited

U.S. PATENT DOCUMENTS

| | | |
|---|---|---|
| 4,491,594 A | 1/1985 | Ogawa |
| 4,499,064 A | 2/1985 | Shive |
| 4,500,524 A | 2/1985 | Catsimpoolas |
| 4,806,354 A | 2/1989 | Green |
| 5,053,396 A | 10/1991 | Blass |
| 5,095,115 A | 3/1992 | Grimmer et al. |
| 5,776,783 A | 7/1998 | Kell |
| 5,885,976 A | 3/1999 | Sandyk |
| 6,068,981 A | 5/2000 | Rittenburg et al. |
| 6,136,801 A | 10/2000 | Kell |
| 6,395,299 B1 | 5/2002 | Babich et al. |
| 6,500,450 B1 | 12/2002 | Hendrix |
| 6,514,544 B2 | 2/2003 | Fuchs et al. |
| 6,589,994 B1 | 7/2003 | Artman et al. |
| 6,835,750 B1 | 12/2004 | Henderson |
| 7,273,884 B2 * | 9/2007 | Shellenberger ............ 514/379 |
| 2002/0198177 A1 | 12/2002 | Horrobin |
| 2003/0012825 A1 | 1/2003 | Kapper |
| 2004/0111129 A1 | 6/2004 | Gliner et al. |
| 2004/0142992 A1 | 7/2004 | Shellenberger |
| 2004/0225198 A1 | 11/2004 | Kazantseva |
| 2005/0038092 A1 | 2/2005 | Fukuda |
| 2005/0119315 A1 | 6/2005 | Fedida |
| 2005/0249823 A1 * | 11/2005 | Murphy et al. ............ 424/692 |

OTHER PUBLICATIONS

Stern Pathophysiology of rest tremor Proc. Int. Cong. Neuro-Genet. Neuro-Ophthalmol. World Fed. Neurol., 2nd (1969), meeting date 1967, vol. 1, pp. 386-389, abstract.*

Langhor et al. Vitamin B1, B2 and B6 deficiency in neurological disorders, Journal of Neurology, Apr. 1981, vol. 225, No. 2, pp. 1432-1459,Germany.

Stolze et al. The gait disorder of advanced essential tremor. Brain. Nov. 2001, vol. 124, No. 11, pp. 2278-2286, especially p. 2284, lines 4-7.

Balbisi, Ebrahim et al., "Riboflavin in Prophylactic Treatment of Migraine", U.S. Pharmacist , May 16, 2006, 5:32-38,Vo. No. 30:05,—a Jobson Publication,Bloomfield, NJ.

Coimbra CG et al., "High Doses of Riboflavin and the Elimination of Red Meat . . . ",Pub Med, Braz J Med Biol Res. Oct. 2003, 1409-17 ,36(10), Ribeirão Preto SP Brasil.

Sandor PS et al., Prophylactic Treatment of Migraine with Beta-Blockers . . . , Pub Med, Headache.Jan. 2000; 30-5, 40 (1), Neurology Dept., CHR Citadelle, Univ. of Leige, Belgium.

Bodner, Ruth A. et al., "Pharmacological Promotion of Inclusion . . . ", PNAS, Mar. 14, 2006, 4246-4251, vol. 103, No. 11, online + Linthicum, MD.

Mayo Clinic, "Treatment of Essential Tremor at Mayo Clinic in Jacksonville, FL", 2005, Mayo Clinic, Jacksonville, Fla.

The Cleveland Clinic Health Information Center, "Drug Treatments for Essential Tremor", The Cleveland Clinic, 2004, Cleveland, Ohio.

McCormick, D.B.. et al., "Ribovlavin", the American Society for Nutritional Sciences (nutrition.org), 2005.

International Essential Tremor Foundation, "Coping With Essential Tremor", (www.essentialtremor.org),2005, Lenexa, Kansas.

WHYVITAMINS.COM, "Vitamin B2-Riboflavin", 2003.

SPRINGBOARD4HEALTH.COM, "Vitamin B-2", 2004.

CLAROCET.COM, "Essential-b Complex" 2005, Medicor Labs Corp.

University of Maryland Medical Center (www.umm.edu), "Coenzyme Q10", 2004, Baltimore, MD.

NETFIT.CO.UK "Vitamin B", 2006.

National Cancer Institute (www.cancer.gov), "Questions and Answers About Coenzyme Q10", 2006, Bethesda, MD.

HOWSTUFFWORKS .COM, "How B Vitamins Work", 2006, Atlanta, GA.

Vitacost (vitacost.com), "Pantothenic Acid", 2006, Boynton Beach, FL.

Essense of Life ,(essense-of-life.com) "Vitamin B", 2005.

(Continued)

Primary Examiner—Jennifer M Kim
(74) Attorney, Agent, or Firm—Gottlieb, Rackman & Reisman

(57) ABSTRACT

Essential tremor can effectively be treated with high doses of Riboflavin (vitamin B2), either on its own or coupled with one or more other B vitamins and/or coenzyme Q10 (CoQ10). The treatment constitutes a significant improvement over prior treatment methods in that it not only alleviates essential tremor, but results in better performance of the affected body portion and may delay the progression of the disease. The preferred addition of other B vitamins and/or CoQ10 also provides balance to the nutrient energy requirements of a patient's body.

8 Claims, No Drawings

OTHER PUBLICATIONS

Bates, CJ et al., "Biochemical Indices and Neuromuscular Function Tests . . . ",BR J Nutr, 1994, 601-10, 72(4), Oxfordshire, U.K.

Haralambie G., "Vitamin B2 status in athletes and the influence of riboflavin . . . ", (inforetrieve.com) Nutr Metab., 1976, 1-8, 20(1), BioMed Central.

Baker, SK et al., "Targeting Cellular Energy Production in Neurological Disorders", (infrotreive.com) Expert Opin Investig Drugs, 2003, -1655-79, 12(10).

National Cancer Institute, "Coenzyme Q10 (PDQ)", 2005, www.cancer.gov.

Bates et al., "Biochemical indices and neuromuscular function tests in rural Gambian schoolchildren . . . ", [Pub Med.—NCBI] Br. J. Nutr., Oct. 1994, pp. 601-610, 72 (4).

Lieberman, "Dr. Lieberman Answers Your Questions, Are Vitamins Good for PD?", 2005, Lieberman Parkinson Clinic, North Bay Village, FL [www.liebermanparkinsonclinic.com].

WholeHealthMD.com, "Riboviavin (Vitamin B2)", 2000, WholeHealthMD , Sterling VA, [WholeHealthMD.com].

* cited by examiner

METHOD OF TREATING NEUROLOGICAL DISORDERS

This application claims priority of U.S. Provisional Application No. 60/705,877 filed Aug. 5, 2005.

BACKGROUND OF THE INVENTION

The present application pertains to neurological disorders, and more specifically, to a neurological disorder generally referred to as essential tremor. Essential tremor is a common but complex neurological movement disorder which typically effects limbs, causing shaking of the arms and hands. Patients may also experience uncontrolled and involuntary shaking of the head, jaw, and the vocal cords, which results in a voice with a quivering quality. It has been associated with hearing loss, balance difficulties, and cognitive problems. There is no known cause and no known cure.

The statistics are alarming. Over age 40, as many as 1 in 20 people may experience essential tremor; over age 65, 1 in 10 people may experience essential tremor. Essential tremor is thought to be 20 times more prevalent than Parkinson's Disease. Although essential tremor does not shorten lifespan, it is associated with significant disability, particularly with fine motor tasks, most prominently eating, drinking, pouring and writing. The disease progressively worsens with time.

There are no medications that have been approved by the Food and Drug Administration for the treatment of essential tremor. The drugs currently in use have been approved for other illnesses and are limited in their effectiveness and by their significant side effects in this population. Clinical studies have been published that showed partial benefit to some patients using beta blockers, anticonvulsants, and benzodiazepines. However, beta blockers cause changes in blood pressure and heart rate, are contraindicated in patients with heart block, asthma, and congestive heart failure, and need to be used with caution in those with diabetes; have side-effects of lightheadedness, depression insomnia, weakness, fatigue, hallucinations to list only a few, which severely limit their use in this relatively older population. Similarly, Primidone [Mysoline], the most commonly prescribed anticonvulsant for essential tremor, can cause acute nausea and vomiting, fatigue, sleepiness, confusion and incoordination to list only a few of its side-effects. Topiramate [Topamax], another anticonvulsant, commonly causes memory and speech abnormalities, and metabolic dysfunction as well as other side effects. Benzodiazepines [Valium, Ativan, Xanax among many others] are controlled substances because of their highly addictive potential and frequently cause sedation, memory impairment and incoordination. Most important of all, these drugs result in a 50% or less improvement of tremor for those some people who respond.

Botulinum Toxin [Botox] has been tried for tremors of the head and hands that fail to respond to the previously listed medications. Because it causes weakness of the trembling site, it interferes with the functioning of those parts, particularly the hand and neck, limiting strength and agility. It is rarely a long term option for most patients.

Surgical procedures have been used in the most severe cases of essential tremor. These procedures involve destroying a part of the brain or implanting electrodes into an area of the brain. These electrodes are then connected to a pacemaker-like battery that stimulates regions of the brain to diminish the tremor. These procedures carry a high risk of stroke, infection and death and if beneficial, only treat one side of this bilateral disease.

Accordingly, existing treatments for neurological disorders such as essential tremor are poorly effective in that they do not stop tremors completely, and in most instances, they do not prevent or even delay the progression of the disease. At the same time, the known treatments have either significant side effects or are associated with considerable risk factors. Thus, it would be desirable to provide a treatment that overcomes these disadvantages.

SUMMARY OF THE INVENTION

It has been discovered that essential tremor can effectively be treated with high doses of riboflavin (Vitamin B2) taken on a daily basis, either on its own or coupled with one or more other B Vitamins and/or coenzyme Q10 (CoQ10). For some patients with severe essential tremor, the combination of riboflavin and currently established medications like beta blockers, anticonvulsants, benzodiazepines and others will act to substantially lessen tremor conditions. The treatment constitutes a significant improvement over prior treatment methods in that it not only alleviates essential tremor, but results in better performance of the affected body portion and may delay the progression of the disease.

Riboflavin is essential to the production of energy by the body. It is critical to the breakdown of carbohydrates, fats and protein; it participates in the metabolism of drugs and toxins, and is a significant cofactor of antioxidant enzymes. The preferred addition of other B Vitamins and/or CoQ10 to the high dose Riboflavin treatment of the invention helps to support these actions.

Accordingly, it is an object of the invention to provide an improved treatment of the neurological disorder known as essential tremor.

Another object of the invention is to provide an improved treatment of essential tremor utilizing high dosages of riboflavin in its various forms, with or without other vitamins and with or without other drugs, such as propranolol, primidone, topiramate, neurontin, zonisamide and others.

A further object of the invention is to provide an improved treatment of essential tremor with minimal side effects.

Still other objectives and advantages will be apparent from the following description.

DETAILED DESCRIPTION OF THE PREFERRED EMBODIMENT

The present invention provides a novel treatment of essential tremor. The treatment consists of an administration of a high dosage of riboflavin, or a riboflavin compound or derivative, either alone or with other B vitamins and/or CoQ10 or other drugs. These compounds can be taken orally in the form of tablets or capsules, as is well known. The compounds can also be taken intramuscularly, intravenously, via patch or by suppository. Also, a sustained release tablet may be utilized.

Riboflavin is a water soluble B Complex Vitamin also known as Vitamin B2. Riboflavin is extremely safe, and, if consumed orally, has no reported toxicity. There are no reports of adverse reactions that can be attributed to Riboflavin consumed orally from food or dietary supplements.

Suitable riboflavin compounds or riboflavin derivatives include:
riboflavinyl glucoside
riboflavin 5' phosphate
riboflavin 5' adenosine diphosphate
riboflavin acid esters
riboflavin butyrate
riboflavin sodium phosphate riboflavin 5'-phosphate sodium
flavinadeninedinucleotide
flavinmononucleotide It has been found that that a dosage of 200 mg to 1000 mg of riboflavin on a daily basis ameliorates the symptoms of essential tremor. A typical riboflavin dosage for a normal adult is between 1 and 2.0 mg. The preferred dosage of riboflavin in accordance with the invention is between about 400 and 800 mg on a daily basis, and even more preferred between 600 and 800 mg on a daily basis.

either hand. Evaluation was based on a four-point scale as published by Fahn, Tolosa and Marin, Clinical Rating Scale for Tremor in *Parkinson's Disease and Movement Disorders* [Williams and Wilkins, 1993].

0=Normal
1=Slight
2=Moderately abnormal
3=Markedly abnormal
4=Severely abnormal

The results are seen in the following table:

| Identifier | Age in years | Gender | Dose (daily) | Tremor Score Before Rx | Tremor Score After Rx | Time on Dose | Side Effects | Concomitant Tremor Medications |
|---|---|---|---|---|---|---|---|---|
| # 1 | 63 | Female | 400 mg | Head 2<br>Hands 1 | Head 1<br>Hands 1 | 6 wks. | None | None |
| # 2 | 74 | Female | 600 mg | Head 2<br>Hands 1 | Head 1<br>Hands 1 | 3 mos. | None | None |
| # 3 | 75 | Female | 400 mg | Head 0<br>R Hand 3<br>L Hand 4 | Head 0<br>R Hand 2<br>L Hand 3 | 4 wks. | None | None |
| # 4 | 75 | Female | 800 mg | Head 0<br>R Hand 2<br>L Hand 3 | Head 0<br>R Hand 2<br>L Hand 2 | 2 wks. | None | None |
| # 5 | 50 | Male | 400 mg | Head 0<br>R Hand 2<br>L Hand 3 | Head 0<br>R Hand 2<br>L Hand 2 | 7 mos. | None | Inderal LA 80 mg. |
| # 6 | 60 | Female | 400 mg | Head 0<br>R Hand 2<br>L Hand 2 | Head 0<br>R Hand 1<br>L Hand 1 | 12 mos. | None | Inderal LA 60 |
| # 7 | 90 | Female | 400 mg | Head 0<br>R Hand 2<br>L Hand 2 | Head 0<br>R Hand 1<br>L Hand 1 | 4 wks. | None | None |
| # 8 | 87 | Male | 600 mg | Head 0<br>R hand 4<br>L hand 4 | Head 0<br>R Hand 3<br>L Hand 3 | 4 wks. | None | Topamax |
| # 9 | 82 | Female | 400 mg | Head 0<br>R Hand 4<br>L Hand 4 | Head 0<br>R Hand 4<br>L hand 3 | 4 wks. | None | Mysoline, Inderal and Topamax |
| # 10 | 82 | Female | 800 mg | Head 0<br>R Hand 4<br>L Hand 3 | Head 0<br>R Hand 4<br>L Hand 2 | 4 mos. | None | Mysoline, Inderal and Topamax |
| # 11 | 88 | Female | 400 mg | Head 2<br>R Hand 2<br>L Hand 2 | Head 1<br>R Hand 1<br>L Hand 1 | 1 year | None | None |
| # 12 | 85 | Male | 400 mg | R hand 2 | Head 2<br>R Hand 1<br>L Hand 2 | 2 wks. | None | None |
| # 13 | 75 | Female | 400 mg | Head 0<br>R Hand 2<br>L Hand 2 | Head 0<br>R Hand 1<br>L Hand 1 | 3 wks. | None | None |
| # 14 | 74 | Male | 400 mg | Head 0<br>R Hand 2<br>L Hand 2 | Head 0<br>R Hand 1<br>L Hand 1 | 5 mos. | None | None |
| # 15 | 66 | Male | 400 mg | Head 0<br>R Hand 1<br>L Hand 2 | Head 0<br>R Hand 1 | 1 mo. | None | None |

If taken orally, riboflavin should preferably be taken two times/per day (once in the morning, once in the evening) in order to achieve a desired daily dosage. It can also be taken as a single dose in the morning or evening, but is preferred at bedtime.

15 persons over the age of 50 were tested, utilizing daily dosages of between 400 and 800 mg of riboflavin. Riboflavin was the only vitamin used for those patients who were on other tremor medications. These patients were continued on them.

Patients were evaluated with arms outstretched, elbows bent and hands near the chin, writing with both hands, drinking holding a cup with either hand, and pouring water with The results of the tests were dramatic: some people who were unable to feed themselves because of the tremors could now manipulate a knife and fork. Other persons had significant improvement, allowing them to write or use their hands in a fashion that was nearly normal. In most patients, a slight tremor that did not interfere with function remained. Within a few days of stopping the daily intake of the high dosage of riboflavin, the symptoms of essential tremor returned.

If included, the dosage of coenzyme Q10 is preferably between about 600 and 2000 mg on a daily basis. The preferred dosage of coenzyme Q10 on a daily basis is between about 1000 and 1600 mg.

The dosages of any additional B vitamins are as follows:

| | |
|---|---|
| Thiamine (Vitamin B-1) | 50-100 mg |
| Niacin (Vitamin B-3) | 20-50 mg |
| Pantothenic Acid (Vitamin B-5) | 50-100 mg |
| Pyridoxine (Vitamin B-6) | 25-50 mg |
| Folic Acid (Vitamin B-9) | 1-4 mg |

For one patient, before beginning a course of therapy in accordance with the inventive treatment, that patient's tremor score was Head 0, Right Hand 2, Left Hand 3. Treatment commenced for three months as follows:

| | |
|---|---|
| Riboflavin | 400 mg per daily dosage |
| Coenzyme Q10 | 1000 mg per daily dosage |
| Thiamine | 50 mg per daily dosage |
| Niacin | 50 mg per daily dosage |
| Pantothenic Acid | 50 mg per daily dosage |

The tremor score, after three months of treatment, improved to Head 0, Right Hand 1, Left Hand 2. Treatment then continued for an additional three months with an increase in the daily dosage of Riboflavin to 800 mg. The tremor score was then measured to be Head 0, Right Hand 0, Left Hand 1. Treatment then continued for an additional three months with just daily dosages of Riboflavin (800 mg) and coenzyme Q10 (1000 mg) with stable head and hand findings following treatment. Thereafter, for a period of a year, treatment continued with just Riboflavin at a daily dosage of 800 mg—stable head and hand findings continued to be exhibited. It was noted, however, that if treatment was missed for two days or more, prior untreated levels of tremor returned. Moreover, if treatment was resumed, there was a return to reduced tremor levels after 2 to 3 days.

Dosages are easily adjusted for patients having specific requirements, including overweight or underweight patients. The only side effect is bright yellow urine.

Other conditions that are commonly seen in patients with essential tremor, such as deafness, motion sickness, balance difficulties, and cognitive problems may be benefited by this treatment. Additionally, patients who develop tremors due to the use of medications that cause tremor (such as Depakote and Lithium) may benefit by the use of the inventive vitamin therapy. In that regard, one patient with severe epilepsy on high dose Depakote that resulted in tremor on action and intention, was treated with the inventive vitamin therapy. Her tremor significantly improved and as an additional benefit, her seizure frequency decreased. Prior to the Riboflavin treatment, the patient had seizures when she had colds or fever; during the treatment, even though the patient suffered from one or more colds, the patient did not also experience the seizures. Other neurological conditions, such as epilepsy, when associated with tremor, may be benefited by the inventive vitamin therapy.

Other movement disorders may benefit from the inventive treatment with some variation in the levels of the various vitamins being given. Also, other disorders affecting hearing and balance may also benefit from the inventive treatment.

Thus, it was found that the treatment presented herein was very effective for ameliorating the existing symptoms of essential tremor and in delaying the progression of more severe symptoms. Moreover, as is well known in the art, the compounds used for the treatment in accordance with the invention have no significant side effects.

It will thus be seen that the objects set forth above, among those made apparent from the preceding description, are efficiently obtained, and since certain changes may be made in carrying out the above method without departing from the spirit and scope of the invention, it is intended that all matter contained in the above description shall be interpreted as illustrative and not in a limiting sense.

It is also to be understood that the following claims are intended to cover all the generic and specific features of the invention herein described and all statements of the scope of the invention, which as a matter of language, might be said to fall there between.

The invention claimed is:

1. A method for treating essential tremor in a human being comprising administering to said being a pharmaceutically effective amount of a composition selected from the group consisting of riboflavin, riboflavinyl glucoside, riboflavin 5' phosphate, riboflavin 5' adenosine diphosphate, riboflavin acid esters, riboflavin butyrate, riboflavin sodium phosphate, riboflavin 5'-phosphate sodium, flavinadeninedinucleotide and flavinmononucleotide in an amount between about 200 mg and 1000 mg per daily dosage.

2. The method of claim 1, wherein said composition further includes one or more B vitamins selected from the group consisting of:
   Thiamine, in an amount between about 50 and 100 mg;
   Niacin, in an amount between about 20 and 50 mg;
   pantothenic acid, in an amount between about 50 and 100 mg;
   pyridoxine, in an amount between about 25 and 50 mg; and
   folic acid in an amount between about 1 and 4 mg;
   said amounts being per daily dosage.

3. The method of claim 1, wherein the composition further includes coenzyme Q10 in a daily dosage amount of between about 600 and 2000 mg.

4. The method of claim 1, wherein said composition is administered in a manner selected from the group consisting of orally, intramuscularly, intravenously, via suppository and via a patch.

5. The method of claim 1, wherein the daily dosage of said composition is between about 400 and 800 mg.

6. The method of claim 3, wherein the daily dosage of coenzyme Q10 is between about 1000 and 1600 mg.

7. The method of claim 1, further including the step of administering to said being on a daily basis a pharmaceutically effective amount of a composition selected from the group consisting of beta-blockers, anticonvulsants, and benzodiazepines.

8. The method of claim 2, wherein the composition further includes coenzyme CoQ10 in a daily dosage amount of between about 600 and 2000 mg.

* * * * *